United States Patent
Bonnekessel et al.

(10) Patent No.: US 8,709,751 B2
(45) Date of Patent: Apr. 29, 2014

(54) PREPARATION OF ISOMERICALLY PURE SUBSTITUTED CYCLOHEXANOLS

(75) Inventors: Melanie Bonnekessel, Ludwigshafen (DE); Klaus Ditrich, Gönnheim (DE); Jürgen Däuwel, Heidelberg (DE); Achim Sorg, Mannheim (DE); Wolfgang Ladner, Fussgönheim (DE); Bryan Cooper, Mannheim (DE); Rene Backes, Lampertheim (DE)

(73) Assignee: BASF SE, Ludwigshafen (DE)

( * ) Notice: Subject to any disclaimer, the term of this patent is extended or adjusted under 35 U.S.C. 154(b) by 88 days.

(21) Appl. No.: 13/303,887

(22) Filed: Nov. 23, 2011

(65) Prior Publication Data

US 2012/0135483 A1    May 31, 2012

Related U.S. Application Data

(60) Provisional application No. 61/417,296, filed on Nov. 26, 2010.

(51) Int. Cl.
*C12P 1/00* (2006.01)
*C12P 7/22* (2006.01)

(52) U.S. Cl.
USPC ............................................. 435/41; 435/156

(58) Field of Classification Search
None
See application file for complete search history.

(56) References Cited

U.S. PATENT DOCUMENTS 5,714,642 A * 2/1998 Didion et al. ................. 568/810
6,596,520 B1   7/2003 Friedrich et al.

2007/0128704 A1   6/2007 Sturmer

FOREIGN PATENT DOCUMENTS

EP     1069183 A2      1/2001
WO     WO-2005/073215 A1   8/2005

OTHER PUBLICATIONS

Kahlow et al. (A model of the pressure dependence of the enantioselectivity of *Candida rugosa* lipase towards (±)-menthol Protein Science (2001), 10:1942-1952).*
Sanchez et al. (Continuous enantioselective esterification of trans-2-phenyl-1-cyclohexanol using a new *Candida rugosa* lipase in a packed bed bioreactor, Journal of Biotechnology 84 (2000), 1-12).*
Yang et al. (Ann N Y Acad Sci. Oct. 12, 1996;799:358-63, Enhancing the stereoselectivity and activity of *Candida* species lipase in organic solvent by noncovalent enzyme modification).*
Giuseppin et al. (WO9100920-A. published Jan. 24, 1991).*
Frenken et al. (Cloning of the *Pseudomonas glumae* lipase gene and determination of the active site residues, Appl. Environ. Microbiol. 58 (12), 3787-3791 (1992)).*

* cited by examiner

*Primary Examiner* — Suzanne M Noakes
*Assistant Examiner* — Jae W Lee
(74) *Attorney, Agent, or Firm* — Novak Druce Connolly Bove + Quigg LLP

(57) ABSTRACT

The present invention relates to the preparation of isomerically pure substituted cyclohexanols starting from a mixture of cis/trans substituted cyclohexanols which comprises reacting the cis/trans mixture of a substituted cyclohexanol with a dicarboxylic acid anhydride in the presence of a lipase, to give the trans semi-ester which is separated off from the unreacted substituted cyclohexanol cis isomer.

14 Claims, No Drawings

PREPARATION OF ISOMERICALLY PURE SUBSTITUTED CYCLOHEXANOLS

CROSS-REFERENCE TO RELATED APPLICATIONS

This application claims benefit under 35 U.S.C. §119(e) of U.S. Provisional Patent App. Ser. No. 61/417,296, filed Nov. 26, 2010, which is incorporated herein by reference in its entirety.

SEQUENCE LISTING

The Sequence Listing associated with this application is filed in electronic format via EFS-Web and is hereby incorporated by reference into the specification. The name of the text file containing the Sequence Listing is SEQUENCE_LISTING__12810-01300_ST25.txt. The size of the text file is 10 KB, and the text file was created on Nov. 23, 2011.

The present invention relates to a process for preparing substantially isomerically pure substituted cyclohexanols starting from a mixture of cis/trans substituted cyclohexanols.

Separating mixtures of cis/trans isomers can be achieved by using various techniques known to those skilled in the art e.g., distillation, chromatography, crystallization.

WO 2005/073215 describes a method for producing enantiomerically pure amino-alcohols. It discloses that enantioselective acylation of a racemic alcohol with succinic anhydride in the presence of a lipase gives a succinic semi-ester, which can be separated from the unreacted enantiomer.

EP 1069183 A2 teaches the enantioselective acylation of racemic trans-2-methoxycyclohexanol by succinic anhydride in the presence of an immobilized lipase from *Pseudomonas burkholderia*.

Often distillative separation is used for separation of cis/trans isomers. However, in the case of substituted cyclohexanols this method was unsatisfactory because of the sublimation characteristics of substituted cyclohexanols. Therefore, the technical problem to be solved was to find a method for separating a mixture of cis/trans substituted cyclohexanols.

The present invention solves the problem by providing a process for separating substituted cyclohexanols in substantially isomerically pure forms, which comprises
  (i) reacting the cis/trans mixture of the substituted cyclohexanol with a dicarboxylic acid anhydride in the presence of a lipase with a protein sequence as displayed in SEQ ID No:2 or a lipase with a protein sequence being at least 75% identical to the entire amino acid sequence shown in SEQ ID No:2 and have at least 50% of the enzymatic activity of SEQ ID No:2, to give the trans semi-ester,
  (ii) separating off the trans semi-ester from the unreacted substituted cyclohexanol cis isomer,
  (iii) isolating the isomerically pure substituted cis or trans cyclohexanol.

Surprisingly, the lipase used in the inventive process triggers with high selectivity the acylation of the trans form of substituted cyclohexanols by the dicarboxylic-acid anhydride. As a result of the inventive process the cis or trans isomer of the substituted cyclohexanol is gained in substantially isomerically pure form.

"Substantially isomerically pure" means that the cis or trans product is not substantially contaminated with the other isomer. Therefore, "substantially isomerically pure" means that the isomer is gained in at least 80%, preferably at least 90%, more preferably at least 95%, in particular at least 96, 97, 98, 99%.

The first step of the inventive process:

The cis/trans mixture of the substituted cyclohexanols (formula A1 to A3 below) is reacted with a dicarboxylic-acid anhydride in the presence of a lipase with a protein sequence as displayed in SEQ ID No:2 or a lipase with a protein sequence being at least 75% identical to the entire amino acid sequence shown in SEQ ID No:2 and have at least 50% of the enzymatic activity of SEQ ID No:2, to give a semi-ester (formula C1 to C3 below) and the unreacted isomer (formula B1 to B3 below). Notably, the trans isomer is selectively acylated by using the said lipase.

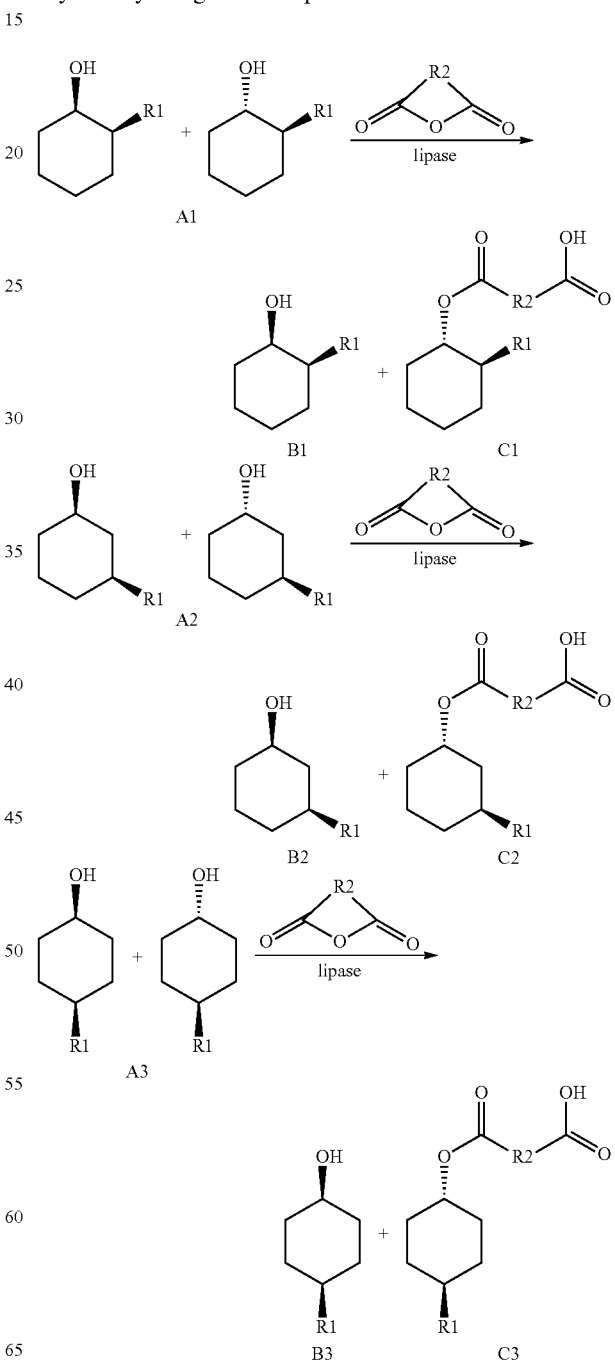

In a preferred embodiment, the starting material is a cis/trans mixture of 4-substituted cyclohexanols (formula A3 above), which is reacted with a dicarboxylic-acid anhydride in the presence of a lipase with a protein sequence as displayed in SEQ ID No:2 or a lipase with a protein sequence being at least 75% identical to the entire amino acid sequence shown in SEQ ID No:2 and have at least 50% of the enzymatic activity of SEQ ID No:2, to give a semi-ester (formula C3 above) and the unreacted isomer (formula B3 above).

The substituted cyclohexanols used in the process of the invention according to formula A1 to A3 are substituted by R1. R1 can be any substituent being inert under the reaction conditions.

For example, R1 can be substituted or unsubstituted $C_1$-$C_{10}$ alkyl, substituted or unsubstituted $C_3$-$C_8$-cycloalkyl, substituted or unsubstituted $C_2$-$C_{10}$-alkenyl or alkynyl, substituted or unsubstituted heterocycle, substituted or unsubstituted aryl.

"Unsubstituted $C_1$-$C_{10}$" refers to a straight-chained or branched saturated hydrocarbon group having 1 to 10 carbon atoms, for example methyl, ethyl, propyl, 1-methyl-ethyl, butyl, 1-methylpropyl, 2-methylpropyl, and 1,1-dimethylethyl etc. These are substituents called unsubstituted in the context of the invention.

The term "unsubstituted $C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

"Unsubstituted $C_2$-$C_{10}$ alkenyl" refers to a straight-chain or branched unsaturated hydrocarbon radical having 2 to 10 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl etc. Also included in this definition for the purpose of this invention are cyclic unsaturated hydrocarbon radicals having 5 to 8 carbon ring members such as cyclopentadienyl, cyclohexadienyl, cycloheptadienyl, cyclooctadienyl.

The term "$C_2$-$C_{10}$-alkynyl" refers to a straight-chain or branched unsaturated hydrocarbon radical having 2 to 10 carbon atoms and containing at least one triple bond, such as ethynyl, 1-propynyl, 2-propynyl (propargyl), 1-butynyl, 2-butynyl, 3-butynyl, 1-methyl-2-propynyl etc.

The term heterocycle means e.g. "5-, 6-, or 7-membered heterocycles" wherein the ring member atoms of the heterocycle include besides carbon atoms 1, 2, 3 or 4 heteroatoms selected from the group of N, O and S, is to be understood as meaning both saturated and partially unsaturated as well as aromatic heterocycles (i.e. heteroaryl). Examples include:

saturated and partially unsaturated 5-, 6-, or 7-membered heterocycle wherein the ring member atoms of the heterocycle include besides carbon atoms 1, 2 or 3 heteroatoms selected from the group of N, O and S, and which is saturated or partially unsaturated, for example pyrrolidin-2-yl, pyrrolidin-3-yl, tetrahydrofuran-2-yl, tetrahydrofuran-3-yl, tetrahydrothien-2-yl, tetrahydrothien-3-yl, 1,3-dioxolan-4-yl, isoxazolidin-3-yl, isoxazolidin-4-yl, isoxazolidin-5-yl, isothiazolidin3-yl, isothiazolidin-4-yl, isothiazolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 2-pyrrolin-2-yl, 2-pyrrolin-3-yl, 3-pyrrolin-2-yl, 3-pyrrolin-3-yl, piperidin-2-yl, piperidin-3-yl, piperidin-4-yl, 1,3-dioxan-5-yl, tetrahydropyran-2-yl, tetrahydropyran-4-yl, tetrahydrothien-2-yl, hexahydropyridazin-3-yl, hexahydropyridazin-4-yl, hexahydropyrimidin-2-yl, hexahydropyrimidin-4-yl, 5-hexahydropyrimidinyl and piperazin-2-yl;

5-membered heteroaryl (heteroaromatic radical), wherein the ring member atoms of the heteroaryl include besides carbon atoms 1, 2 or 3 heteroatoms selected from the group of N, O and S, for example pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl-1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl;

6-membered heteroaryl (heteroaromatic radical), wherein the ring member atoms of the heteroaryl include besides carbon atoms 1, 2 or 3 heteroatoms selected from the group of N, O and S, for example pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl.

"Unsubstituted aryls" in particular are phenyl, naphthyl, anthryl or phenanthryl.

"Substituted" in the context of the invention means here, by comparison with the corresponding unsubstituted substituent, one or more H atoms are replaced by other atoms or molecular groups being inert in the inventive process, such as alkyl, N(alkyl)$_2$, O-alkyl, S-alkyl, CN, NO$_2$, I, Cl, Br, F, carbonyl, carboxyl, COOR3 with R3 being alkyl, 5-, 6-, or 7-membered heterocycle, aryl—the latter two as defined above. In the context of inert substitutents, "alkyl" means $C_1$-$C_{10}$-alkyl being a straight-chained or branched saturated hydrocarbon group having 1 to 10 carbon atoms, such as methyl, ethyl, propyl, isopropyl, butyl, isobutyl etc.

The lipase-catalyzed acylation reaction of the invention requires the use of a dicarboxylic-acid anhydride. In principal every dicarboxylic-acid anhydride e.g. see formula D

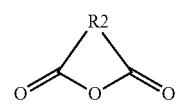

D can be used for that purpose. Preferably, R2 is $C_2$-$C_{10}$ Alkyl. Examples for dicarboxylic acids to be used for the process of the invention are: propanedioic (i.e. malonic) acid anhydride, butanedioic (i.e. succinic) acid anhydride, pentanedioic (i.e. glutaric) acid anhydride, hexanedioic (i.e. adipic) acid anhydride, heptanedioic (i.e. pimelic) acid anhydride, octanedioic (i.e. suberic) acid anhydride, nonanedioic (i.e. azelaic) acid anhydride, decanedioic (i.e. sebacic) acid anhydride, undecandioic acid anhydride, dodecandioic acid anhydrid. Particular preference is given to using $C_3$-$C_8$ dicarboxylic anhydrids, e.g. succinic acid anhydride.

The dicarboxylic-acid anhydride used in the inventive process is used preferably in equimolar amounts, more preferably in at least 10% excess to allow total acylation of the trans isomer. The composition of the starting material, i.e. the percentage of trans-isomer in the mixture of cis/trans substituted cyclohexanol, is decisive for deciding about the amount of dicarboxylic-acid anhydride used in the process of the invention. For example for a 30:70 mixture of cis/trans isomers the use of 0.7 equivalents or in excess of 0.8 equivalents of dicarboxylic-acid anhydride should serve the purpose of nearly totally acylating the trans substituted cyclohexanol.

The lipase used in the inventive process is chosen from lipases having an amino acid sequence according to SEQ ID No:2 or a sequence derived from that displayed as SEQ ID No:2 showing up to 25%, preferably up to 20%, more preferably up to 15% in particular up to 10, 9, 8, 7, 6, 5, 4, 3, 2, 1% of the amino acid residues changed by deletion, substitution, insertion or a combination thereof. That means, that lipases used in the inventive process have sequences that are at least 75%, preferably at least 80%, more preferably at least 85% in particular at least 90, 91, 92, 93, 94, 95, 96, 97, 98, 99% identical to the entire amino acid sequence displayed in SEQ ID No:2. The percent sequence identity between two sequences is a function of the number of identical positions shared by the sequences (i.e., percent sequence identity=numbers of identical positions/total numbers of positions×100).

The lipase used in the inventive process can be expressed in a lipase producing organism. A lipase producing organism means any organism which is able by nature or through genetic modification, for example by insertion of a lipase gene into the genome of the organism, to produce a lipase having an amino acid sequence according to SEQ ID No:2 or a sequence that is at least 75%, preferably at least 80%, more preferably at least 85% in particular at least 90, 91, 92, 93, 94, 95, 96, 97, 98, 99% identical to the entire amino acid sequence displayed in SEQ ID No:2. Examples for lipase producing organisms are microorganisms of the genus *Aspergillus, Arthrobacter, Alcaligenes, Bacillus, Brevibacterium, Pseudomonas, Chromobacterium, Candida, Fusarium, Geotrichum, Humicola, Mucor, Pichia, Penicillium, Rhizomucor, Rhizopus* or *Thermus*. Preferred is the expression in *Pseudomonas burkholderia* (i.e. *Burkholderia plantarii*).

The preferred lipase gene inserted into the lipase producing organism is a) the polynucleotide as defined in SEQ ID No:1, b) a polynucleotide at least about 50%, preferably at least about 60%, more preferably at least 70%, 75%, 80%, 85% or 90%, and even more preferably at least 95%, 96%, 97%, 98%, 99% or more identical to the sequence of SEQ ID No:1 over the entire length of the coding region of the sequence of SEQ ID No:1. The percent sequence identity between the two sequences is a function of the number of identical positions shared by the sequences (i.e., percent sequence identity=numbers of identical positions/total numbers of positions×100).

The cultivation of a lipase-producing organism can take place in a manner known per se, for example by fermentation in a nutrient medium which, besides nutrients, trace elements and, where appropriate, antibiotics, contains, for example, a buffer system to stabilize the proteins and enzymes. Cultivation of a lipase producing organism is described e.g. in U.S. Pat. No. 6,596,520 B1, especially Example 1 paragraph 1.1. where *Burholderia plantarii* is used as an example.

Compared to SEQ ID No:2 the derived amino acid sequences used in the inventive process shall have at least 50%, preferably 65%, more preferably 80%, in particular more than 90% of the enzymatic activity of SEQ ID No:2. In this context, enzymatic activity of SEQ ID No:2 means the ability to trigger the trans-selective acylation of the substituted cyclohexanol. The trans-selectivity is at least 95%, more preferably at least 98%, even more preferably 99%. As reference substance 4-tert.-butyl-cyclohexanol can be used.

The lipase activity per se can be determined by known methods (Gupta et al. Review: Lipase assays for conventional and molecular screening: an overview, Biotechnol. Appl. Biochem. (2003) 37, 63-71). In aqueous medium the catalytic activity is preferably measured by using the Tributyrin-test. In organic systems the Phenylethanol-test is applicable.

Failure to fold into the intended 3-dimensional shape usually produces inactive proteins or enzymes. The folding often takes place under the supervision of specialized molecules, called folding-helper proteins. In one preferred embodiment
the lipase having an amino acid sequence according to SEQ ID No:2 or a sequence that is at least 75%, preferably at least 80%, more preferably at least 85% in particular at least 90, 91, 92, 93, 94, 95, 96, 97, 98, 99% identical to the entire amino acid sequence displayed in SEQ ID No:2 is encoded by
the polynucleotide as defined in SEQ ID No:1, or a polynucleotide at least about 50%, preferably at least about 60%, more preferably at least about 70%, 75%, 80%, 85% or 90%, and even more preferably at least about 95%, 96%, 97%, 98%, 99% or more identical to the sequence of SEQ ID No:1 over the entire length of the coding region of the sequence of SEQ ID No:1 which is expressed in
*Burkholderia plantarii*.

Consequently, in *Burkholderia plantarii* a folding-helper protein having an amino acid sequence according to SEQ ID No:3 or a sequence derived from that displayed as SEQ ID No:3 being at least 85% in particular at least 90, 91, 92, 93, 94, 95, 96, 97, 98, 99% identical to the entire amino acid sequence displayed in SEQ ID No:3 is co-expressed with the lipase.

The lipases used in the process of the invention can be employed as crude extract of whole cells and in preparations of varying purity (e.g. cell-free extract) up to a highly purified form. Preference is given to using the lipases in the form of partially purified or highly purified protein solutions. *Burkholderia plantarii* cells used in the preferred embodiment are small with having a specific density which is comparable to that of the culture medium. Preferably they are separated from the supernatant by microfiltration using appropriate filter plates and strong pumps as known to those skilled in the art. Further concentration can be achieved e.g. by using ultrafiltration as known to those skilled in the art.

From lipases used in solution for converting substrates, immobilized lipases are distinguished which usually have increased stability and are useful for carrying out the reaction continuously and batchwise. Immobilized means carrier-bound on a usually solid support, using methods known to the skilled person, and then employed in the process according to the invention (see below). Using immobilized lipases is a preferred embodiment particularly when conducting the process continuously. For this purpose, the lipases can e.g. advantageously be used while being retained in a column or a tubular reactor.

Various possibilities are available to immobilize the lipase used in the process of the invention. The crude extract of a whole cell suspension or the supernatant of a cell culture, as well as purified protein solutions can be immobilized according to methods like those described in e.g. Persson et al. Biotechnology Letters 2000, 22(19): 1571-1575; U.S. Pat. No. 6,596,520 B1—especially example 1.

Also, the cultivation medium (or fermentation liquor) of a lipase producing organism can be spray-dried itself at temperatures (outlet temperature of the spray drier) of 50-150° C., preferably 70-100° C., more preferably 75-85° C. and even more preferably at 80-85° C. Spray-drying can also occur in the presence of carrier substances. The carrier must be chosen in a way that the process of the invention can take place. Preferably, polysaccharides like e.g. maltodextrine or mineral compounds like e.g. $Na_2SO_4$ are used as carriers. The weight amount of carrier is 5 to 200% per weight, preferably 10-200% by weight, more preferably 20-150% by weight and particularly preferably 50-100% by weight, based on the solid content of the fermentation liquor. Also, purified lipase solution can be immobilized with such methods. The residual moisture is less than 10%, based on solid substance, preferably it is less than 7%, particular preference being given to residual moisture content of less than 5%.

In the process of the invention the (immobilized) lipase is used in amounts of 0.5-10% by weight with respect to the starting material (cis/trans mixture), preferably 0.5-5% by weight, more preferably 0.5-1, in particular 1% by weight.

The acylation reaction of the invention can take place without or in the presence of a solvent. Preferably it takes place in an organic solvent, such as a hydrocarbon, an ether, or an alcohol. Solvents which are particularly suitable for the reaction are:

aliphatic hydrocarbons such as hexane, heptane and octane or a mixture thereof, especially petrolether, or aromatic hydrocarbons like benzene, toluene, xylenes, or ethers such as methyl-tert.-butylether (MTBE), tetrahydrofurane (THF), 1,4-dioxane, or cycloaliphatics like cyclopentane, cyclohexane, or tertiary alcohols like tert.-butylalcohol, tert.-amylalcohol.

If a solvent is used, the starting material (cis/trans mixture) is diluted with an organic solvent such that a 0.2-5 molar solution, preferred 0.5-2 molar, more preferred in 0.6-1.2 molar of the starting material (cis/trans mixture) results.

The reaction can be carried out either continuously or batchwise. Continuous synthesis, especially using a supported lipase, is recommended for performance on the industrial scale.

The second step of the inventive process:

The mixture of semi-ester and unreacted isomer requires the separation of the semi-ester from the unreacted isomer. This is expediently achieved by aqueous extraction, e.g. aqueous extraction, of the semi-ester salt, in particular its alkali or earth alkali metal salt. A preferred embodiment is the aqueous extraction in the presence of a base such as sodium carbonate or sodium hydroxide. Preferably the pH should for this reason be in a range of 7.5-10, preferably 8-10, more preferably 8-9.5, in particular 9-9.5.

The third step of the inventive process:

Depending on which isomer of the alcohol is required, either the organic phase, which contains the cis isomer, or the aqueous phase, which contains the trans isomer in form of the semi-ester, can be worked up. Customary methods of hydrolysis can be used to cleave the semi-ester into the corresponding acid and the desired trans-isomer of the alcohol e.g. by treatment with bases (e.g. NaOH, KOH, $Na_2CO_3$) or acids (e.g. $H_2SO_4$, HCl).

Below, the invention is further described by the examples given. This illustration is by no means meant to be limiting for the invention.

EXAMPLE 1

Preparation of a Shake-Flask Preculture

Two 1000 ml Erlenmeyer flasks were sealed with cotton wool plugs, covered with aluminum foil and sterilized for 30 min at 134° C. A 250 ml graduated glass cylinder was sealed with aluminum foil and likewise sterilized for 30 min at 134° C.

A microelement salt solution was prepared with the following components: two liters of fully demineralized water, 77.2 g of citric acid monohydrate, 22.6 g of zinc sulfate heptahydrate, 17.3 g of diammonium iron(II) sulfate hexahydrate, 5.7 g of manganese sulfate monohydrate, 1.2 g of copper sulfate pentahydrate, 0.5 g of cobalt sulfate heptahydrate and 3.0 g of calcium chloride dihydrate.

500 ml of medium comprising the following components were made up: 3.8 g of dry yeast extract powder, 0.5 g of potassium dihydrogen phosphate, 1.5 g of diammonium hydrogen phosphate, 0.5 g of magnesium sulfate heptahydrate, 5 g of trace element salt solution per 500 g of water. The pH was brought to 6.5 using phosphoric acid. The finished medium was filter-sterilized (0.22 μm). 200 ml of the medium were transferred aseptically into each of the two Erlenmeyer flasks, and the flasks were then inoculated with in each case 1 ml of a Burkholderia plantarii (LU 8093) stock.

The Erlenmeyer flask cultures were then incubated for 12 hours in a shaker-incubator at 30° C. and 200 rpm (orbital radius of the shaker=25 mm).

EXAMPLE 2

Preparation of a Fermenter Preculture 10 liters of the medium specified in Example 1 were made up in a stainless-steel bucket and the pH was brought to 6.5 using phosphoric acid. Then, the medium was transferred into a 21-liter fermenter equipped with three traditional blade agitators. The fermenter was sterilized for 60 minutes at 121° C. and then cooled to 30° C.

The fully-grown Erlenmeyer flask precultures were then aseptically transferred into the prefermenter, and the fermenter was operated for eight hours under the following conditions: aeration rate 0.5 vvm pressurized air, constant temperature of 30° C., overlay pressure=0.1 bar, rotational speed=1000 rpm, pH regulation at 6.5 with 25% strength sodium hydroxide solution and 20% strength phosphoric acid.

EXAMPLE 3

Lipase Production in a Fermenter

A fermenter with a total volume of 300 liters was charged in succession with the following starting materials:

150 liters of fully demineralized water, 1207 g of dry yeast extract powder, 160 g of potassium dihydrogen phosphate, 480 g of diammonium hydrogen phosphate, 432 g of magnesium sulfate heptahydrate, 1600 g of trace element salt solution (of Example 1), 30 ml of Tegosipon® 3062 (silicone-based antifoam). The pH of the medium was adjusted to 4.5 with 20% strength phosphoric acid.

The fermenter was sterilized for 60 minutes at 121° C. and then cooled to 30° C. Then, the fermenter was inoculated aseptically with the preculture of Example 2 and operated under the following conditions: aeration rate 0.4 vvm pressurized air, constant temperature of 30° C., overlay pressure=0.3 bar, rotational speed=550 rpm, pH regulation at 6.5 with 25% strength sodium hydroxide solution and 20% phosphoric acid.

After four hours of fermentation time had elapsed, rapeseed oil was pumped in via a filter-sterilization unit of pore size 0.2 μm. In the first feed phase, feeding was carried out in accordance with the formula:

$$\text{feed rate [g/l]} = 19.7 * e^{(0.11*t)}$$

where t represents the fermentation time in hours.

The first feed phase was terminated after 17 hours. Immediately thereafter, more rapeseed oil was pumped in according to the formula:

feed rate [g/l]=168.6*$e^{(0.0069*t)}$

After 96 hours, the oil feeding was stopped, and the operation of the fermenter continued until the oil in the medium had been consumed. Thereafter, the fermenter was cooled to 4° C. Without further delay, a sample was taken, and the total dry matter of the liquor (DM) and the enzymatic activity (units/ml) were determined. The dry matter content was determined with the aid of an infrared moisture analyzer. The enzymatic activity was measured titrimetrically with tributyrin as the substrate. The amount of liquor which liberates one μmol from butyric acid/min tributyrin was defined as one enzymatic unit.

In the 300-liter fermenter, a dry-matter content of 7.56% was measured, with an enzymatic activity of 10256 U/ml. The fermenter weight was 186.8 kg. The total dry-matter amounted to 14.1 kg. The total enzymatic activity amounted to 1916 MU. One MU=1 000 000 units.

EXAMPLE 4

Production of the Immobilized Lipase

The lipase present in the fermentation liquor was immobilized on sodium sulfate by means of spray-drying.

To this end, 14.1 kg of sodium sulfate were added to the fermenter contents and dissolved over one hour at the minimum rotational speed of the fermenter. Thereafter, the entire fermenter content was spray-dried. The spray drier was operated with 250 m³/h nitrogen. The inlet temperature was 180° C. The outlet temperature was 75° C. The fermenter content was injected into the nitrogen stream by means of a two-substance nozzle. The pump speed was adjusted such that the desired outlet temperature was reached (approximately 15 kg/h). The dry powder was separated off via a cyclone and discharged from the cyclone by means of a cell-wheel sluice. A total of 25.6 kg of dry powder were obtained. The residual moisture content of the powder was 1.8%. A sample of the dry powder was dissolved in water and the enzymatic activity was measured using tributyrin. The powder had an activity of 67 360 units/g DM.

The immobilized enzyme catalyzes the following transesterification reaction in the organic medium:

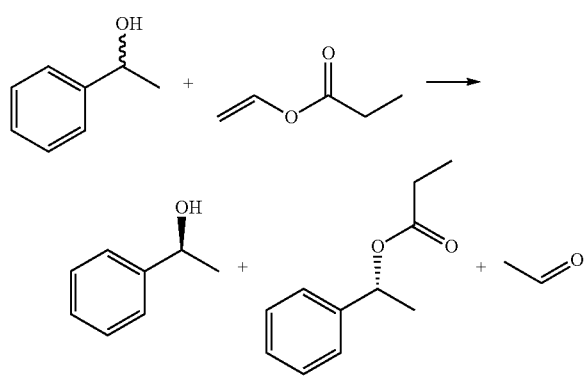

The suitability of the immobilizate for conversions in the organic system was tested as follows: The reaction was carried out in a test reactor composed of a 500 ml jacketed vessel equipped with a propeller agitator made of glass. The agitator was driven by a motor from Heidolph (type RZR 2051) via magnetic coupling. The set-up was heated by a thermostat (Huber Ministat). Approximately 0.5 g of immobilizate were weighed into a 50 ml Falcon® tube and the precise weight was recorded.

The thermostat was set at 22° C. and the stirrer speed to 350 rpm.

Via a glass funnel, the dry reactor was charged with 50.0 g of 1-phenylethanol and 95.0 g of MTBE. Any contamination with water was avoided since too much water prevents the reaction. The pre-weighed lipase-containing immobilizate was added via a glass funnel.

The reaction was started by addition of 20.4 g of vinyl propionate.

60 minutes after the addition of vinyl propionate, a sample (approx. 1 ml) was taken and immediately filtered through a 0.2 μm syringe filter (SPARTAN® 30/02 RC, Schleicher & Schuell). 100 μl of the filtered sample and 900 μl of the HPLC eluent (acetonitrile 20%, methanol 40%, trifluoroacetic acid 1% and water 39%) were placed into a 2 ml Eppendorf® vessel. 100 μl of that solution were in turn placed into an HPLC tube and likewise made up with 900 μl of HPLC eluent, whereupon the tube was sealed. The sample was then analyzed by HPLC.

The unit of the lipase activity in the organic system is PEU (phenylethanol unit). One PEU is the amount of lipase which under the above-described test conditions catalyzes the formation of 1 μmol of phenylethyl propionate (PEP) from phenylethanol per minute.

Parameters Required for the Calculation:

Phenylethyl propionate concentration (PEP) [mmol/l]

Reaction volume [l]

Time (reaction time) [min]

Weight (amount of enzyme employed) [g]

Calculation of the Enzymatic Activity $$\text{Activity}[PEU] = \frac{PEP[\text{mmol}]}{[l]} * \text{reaction volume}[l] * \frac{1000[\mu\text{mol}]}{[\text{mmol}]} \Big/ \text{time[min]}$$

$$\text{Spec. activity}[PEU/g] = \frac{\text{activity}[PEU]}{\text{weight}[g]}$$

Calculation of the Specific Activity

The immobilizate obtained in the example had a specific activity of 842 PEU/g immobilizate.

EXAMPLE 5

Preparation of cis-4-tert.-butyl-cyclohexanol

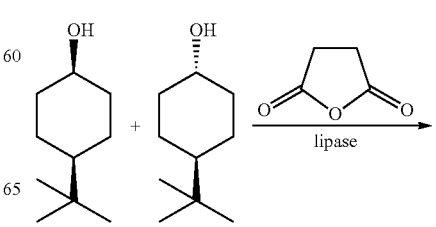

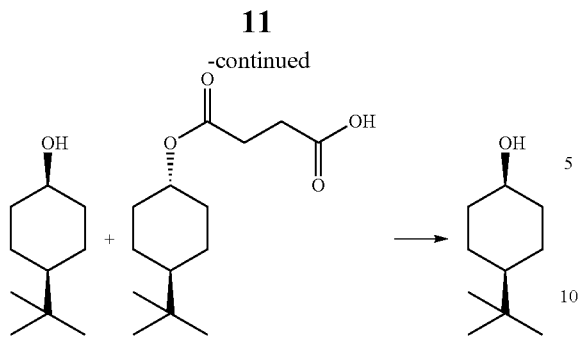

113.4 kg of a cis/trans (30:70) mixture (726 mol, 1 eq) of 4-tert.-butyl-cyclohexanol was introduced into a reaction vessel carrying 453 l MTBE (1.6 mol). 58.1 kg succinic anhydride (580 mol; 0.8 eq) were added as well as 1.1 kg lipase immobilized on $Na_2SO_4$ from *Burkholderia plantarii* (1% per weight; see examples above). The reaction mixture was stirred at 20° C. The reaction process was checked by gas chromatography. As after 23 h reaction time 0.9 GC area % of the trans-isomer were still detected (table 1, No. 3), the reaction mixture was stirred for further 27 h.

TABLE 1 isomeric ratio cis/trans

| No. | probe | Cis (%) | Trans (%) |
|---|---|---|---|
| 1 | Start | 30.6 | 69.4 |
| 2 | After 17 h | 94.6 | 5.4 |
| 3 | After 23 h | 99.1 | 0.9 |
| 4 | After 50 h | 99.9 | 0.1 |

The reaction mixture was filtered via diatomaceous earth (Kieselgur, e.g. Celite®) and the vessel, as well as the MTBE were rinsed with further MTBE. After addition of distilled water to the filtered reaction mixture and to the MTBE-phase of the rinsing step, 25% NaOH solution was added stepwise at 20° C. until a pH of 9.3 was achieved. Further distilled water was added and the phase separation was performed. The aqueous phase (pH 9.3) was extracted another two times with MTBE. The organic phases were combined, and the solvent was removed by distillation (50 mbar, max. 40° C.) until a white suspension was gained. This suspension (109 kg) was further concentrated in a rotating evaporator.

TABLE 2 isomeric ratio cis/trans after extraction

| No. | probe | Cis (%) | Trans (%) |
|---|---|---|---|
| 1 | Org. phases combined | 99.3 | 0.7 |
| 2 | After distillation | 99.6 | 0.4 |

For distillation, a simple distillation apparatus was used with a column carrying packing material (packed column, i.e. Raschigrings, 8×8 mm) and heated solids bridge (tempered condenser). The transition temperature was 118° C. at 26 mbar water-jet vacuum.

Overall, 24.8 kg cis-4-(1,1-Dimethylethyl)-cyclohexanol (73% yield) were gained in form of a white solid.

EXAMPLE 6

Preparation of cis-4-tert.-butyl-cyclohexanol 1 g 4-tert.-Butyl-cyclohexanol (cis/trans 30:70; i.e. 1 eq) was mixed with 10 ml toluene (i.e. 0.6 mol). 0.5 g succinic anhydride (i.e. 0.8 eq) and 0.1 g lipase immobilized on $Na_2SO_4$ were added (i.e. 10% per weight). The reaction conditions were the same as in example 1.

The reaction mixture was stirred for 24 h at 20° C. and further processed as described in example 5. Probes after 1 and 24 h stirring time were analyzed:

| No. | Reaction time | Cis (%) | Trans (%) |
|---|---|---|---|
| 1 | 1 h | 73.2 | 26.8 |
| 2 | 24 h | 100 | — |

EXAMPLE 7

Like Example 6 but Different Solvents (0.6 mol) after 24 h at 20° C.

| No. | solvent | Cis (%) | Trans (%) |
|---|---|---|---|
| 1 | MTBE | 99 | 0.1 |
| 2 | THF | 98 | — |
| 3 | Cyclohexane | 79 | 19 |
| 4 | Petrolether | 81 | 17 |

EXAMPLE 8

Like Example 6 but 1.2 mol Solvent after 24 h at 20° C.

| No. | solvent | Cis (%) | Trans (%) |
|---|---|---|---|
| 1 | MTBE | 100 | — |
| 2 | Toluene | 100 | — |

The invention claimed is:

1. A process for preparing substantially isomerically pure substituted cyclohexanols, comprising:
   (i) reacting a cis/trans mixture of a substituted cyclohexanol with a dicarboxylic acid anhydride in the presence of a lipase to produce a trans semi-ester,
   (ii) separating the trans semi-ester from unreacted substituted cyclohexanol cis isomer, and
   (iii) isolating the substituted cis or trans cyclohexanol, wherein said lipase comprises an amino acid sequence having at least 90% sequence identity to SEQ ID NO: 2 and has the enzymatic activity of SEQ ID NO: 2.

2. The process according to claim 1, wherein said lipase comprises an amino acid sequence having at least 95% sequence identity to SEQ ID NO: 2 and has the enzymatic activity of SEQ ID NO: 2.

3. The process according to claim 2, wherein the lipase is expressed in *Burkholderia plantarii*.

4. The process according to claim 1, wherein said dicarboxylic acid anhydride in step (i) is a C2-C10 dicarboxylic acid anhydride.

5. The process according to claim 4, wherein said C2-C10 dicarboxylic acid anhydride is succinic anhydride.

6. The process according to claim 1, wherein the lipase in step (i) is immobilized.

7. The process according to claim 1, wherein the reaction of step (i) is carried out in a hydrocarbon, an ether, or an alcohol as a solvent.

8. The process according to claim 7, wherein the solvent is toluene, petrolether, MTBE, tetrahydrofurane, or cyclohexane.

9. The process according to claim 1, wherein the separation in step (ii) is carried out by extraction at a pH of 8-10.

10. The process according to claim 1, wherein the cis/trans mixture of the substituted cyclohexanol used is substituted in position 4 related to the OH-group.

11. The process according to claim 10, wherein the substituted cyclohexanol is 4-tert-Butyl-cyclohexanol.

12. The process according to claim 1, wherein said lipase comprises:
    (a) an amino acid sequence encoded by the nucleic acid sequence of SEQ ID NO: 1;
    or
    (b) the amino acid sequence of SEQ ID NO: 2.

13. The process according to claim 1, wherein said lipase is immobilized on a solid support by spray-drying a fermentation liquor comprising said lipase on said solid support.

14. The process according to claim 13, wherein said solid support is $Na_2SO_4$.

* * * * *

SEQUENCE LISTING

<160> NUMBER OF SEQ ID NOS: 3

<210> SEQ ID NO 1
<211> LENGTH: 2562
<212> TYPE: DNA
<213> ORGANISM: Burkholderia plantarii

<400> SEQUENCE: 1

```
gaattcacct tgaacgcagg cgtttcgcgc gcggcgcggc cttcgcgctg cgccgcaata      60
cgtctcgcgc cgtgtcatgt cgattcgcga tgcaatcgtc ggcaatcggc gtgattgttg     120
cgcccgcaac ctgatcgccg cccgcgcccg cgtggcgcgc gcgcggcacg ccattcaccg     180
gatcgatcgc gcccgcttgc gcgccgcagc atccgcgccg tcatatgtcc acccgccgcg     240
cgcgcgcggc gctgtccatc gagtagagac gcctatccaa acggccgtct gattgtagac     300
aggagccgcg ccgccatgtt tcactccgca cttgccgctc gagcgtgccc gacgacctga     360
gaacggcgcg gcgccgcgcg gcgtggcatt ccgatcgacg taaccgataa cgatggagat     420
aaacatggtc agattgatgc gttccagggt ggcggcgagg gcggtggcat gggcgttggc     480
ggtgatgccg ctggccggcg cggccggggtt gacgatggcc gcgtcgcccg ggccgtcgc     540
ggcggacacc tacgcggcga cgcgctatcc ggtgatcctc gtccacggcc tcgcgggcac     600
cgacaagttc gcgaacgtgg tggactattg gtacggaatc cagagcgatc tgcaatcgca     660
tggcgcgaag gtgtacgtcg cgaatctctc gggattccag agcgacgacg ggccgaacgg     720
ccgcggcgag cagctgctcg cctacgtgaa gcaggtgctc gcggccaccg gcgcgaccaa     780
ggtgaacctg atcggccaca gccagggcgg cctgacctcg cgctacgtcg cggccgtcgc     840
gccgcaactg gtggcctcgg tgacgacgat cggcacgccg catcgcggct ccgagttcgc     900
cgacttcgtg caggacgtgc tgaagaccga tccgaccggg ctctcgtcga cggtgatcgc     960
cgccttcgtc aacgtgttcg gcacgctcgt cagcagctcg cacaacaccg accaggacgc    1020
gctcgcggc ctgcgcacgc tcaccaccgc gcagaccgcc acctacaacc ggaacttccc    1080
gagcgcgggc ctgggcgcgc ccggttcgtg ccagacgggc gccgcgaccg aaaccgtcgg    1140
cggcagccag cacctgctct attcgtgggg cggcaccgcg atccagccca cctccaccgt    1200
gctcggcgtg accggcgcga ccgacaccag caccggcacg ctcgacgtcg cgaacgtgac    1260
cgacccgtcc acgctcgcgc tgctcgccac cggcgcggtg atgatcaatc gcgcctcggg    1320
gcagaacgac gggctcgtct cgcgctgcag ctcgctgttc gggcaggtga tcagcaccag    1380
ctaccactgg aaccatctcg acgagatcaa ccagctgctc ggcgtgcgcg cgccaacgc    1440
ggaagatccg gtcgcggtga tccgcacgca cgtgaaccgg ctcaagctgc agggcgtgtg    1500
atggcgcagg ccgatcgtcc ggcgcgcggc gggctggccg cgcgcccgat gcgcggcgcg    1560
tcgttcgcgc tggccgggct cgtcgcgtgt gccgcctgtg ccgcggtcgt gctgtggctt    1620
cggcccgccg ccccgtcgcc cgcgccggcc ggcgccgtcg cgggcgggcc ggcggccggc    1680
gtgcccgccg cggcaagcgg cgcggcggag gccgccatgc cgttgccggc ggcgctgccg    1740
ggcgcgctgg ctggctcgca tgcgccgcgc ctgccgctgg ccgccggcgg ccggctcgcg    1800
aggacgcgcg cggtgcgcga gttcttcgac tattgcctga ccgcgcaggg cgaactgacg    1860
cccgccgcgc tcgatgcgct ggtgcggcgc gagatcgccg cgcagcttga cggcagcccc    1920
gcgcaagcgg aggcgctcgg cgtctggcgc cgctatcgcg cctacttcga cgcgctcgcg    1980
caattgcccg cgcgacggcgc ggtgctcggc gacaagctcg atccggccgc catgcagctc    2040
gcgctcgatc agcgcgcggc gctggccgac cgcacgctcg gcgagtgggc cgagccgttc    2100
ttcggcgacg agcagcgccg gcagcgccat gacctcgaac ggatccggat cgccaacgac    2160
accacgctga gccctgagca gaaggccgcg cggcttgccg cgctcgacgc gcagctgacg    2220
ccggacgagc gcgcgcagca ggcggcgctg catgcgcagc aggacgcggt gacgaagatc    2280
gccgacttgc agaaggccgg cgcgacgccc gaccagatgc gcgcgcagat cgcgcagacg    2340
ctcgggcccg aggcggccgc gcgcgccgcg cagatgcagc aggacgacga ggcgtggcag    2400
```

```
acgcgctatc aagcctatgc ggccgagcgc gaccggatcg cggcgcaggg gctcgcgccg   2460
caggatcgcg atgcgcggat cgcgcagctc aggcagcaga ctttcacggc gccgggggag   2520
gcgatccgcg cggcgtcgct cgatcgcggc gcgggcggtt ag                      2562

<210> SEQ ID NO 2
<211> LENGTH: 358
<212> TYPE: PRT
<213> ORGANISM: Burkholderia plantarii

<400> SEQUENCE: 2

Met Val Arg Leu Met Arg Ser Arg Val Ala Ala Arg Ala Val Ala Trp
1               5                   10                  15

Ala Leu Ala Val Met Pro Leu Ala Gly Ala Ala Gly Leu Thr Met Ala
            20                  25                  30

Ala Ser Pro Ala Ala Val Ala Ala Asp Thr Tyr Ala Ala Thr Arg Tyr
        35                  40                  45

Pro Val Ile Leu Val His Gly Leu Ala Gly Thr Asp Lys Phe Ala Asn
    50                  55                  60

Val Val Asp Tyr Trp Tyr Gly Ile Gln Ser Asp Leu Gln Ser His Gly
65                  70                  75                  80

Ala Lys Val Tyr Val Ala Asn Leu Ser Gly Phe Gln Ser Asp Asp Gly
                85                  90                  95

Pro Asn Gly Arg Gly Glu Gln Leu Leu Ala Tyr Val Lys Gln Val Leu
            100                 105                 110

Ala Ala Thr Gly Ala Thr Lys Val Asn Leu Ile Gly His Ser Gln Gly
        115                 120                 125

Gly Leu Thr Ser Arg Tyr Val Ala Ala Val Ala Pro Gln Leu Val Ala
    130                 135                 140

Ser Val Thr Thr Ile Gly Thr Pro His Arg Gly Ser Glu Phe Ala Asp
145                 150                 155                 160

Phe Val Gln Asp Val Leu Lys Thr Asp Pro Thr Gly Leu Ser Ser Thr
                165                 170                 175

Val Ile Ala Ala Phe Val Asn Val Phe Gly Thr Leu Val Ser Ser Ser
            180                 185                 190

His Asn Thr Asp Gln Asp Ala Leu Ala Ala Leu Arg Thr Leu Thr Thr
        195                 200                 205

Ala Gln Thr Ala Thr Tyr Asn Arg Asn Phe Pro Ser Ala Gly Leu Gly
    210                 215                 220

Ala Pro Gly Ser Cys Gln Thr Gly Ala Ala Thr Glu Thr Val Gly Gly
225                 230                 235                 240

Ser Gln His Leu Leu Tyr Ser Trp Gly Gly Thr Ala Ile Gln Pro Thr
                245                 250                 255

Ser Thr Val Leu Gly Val Thr Gly Ala Thr Asp Thr Ser Thr Gly Thr
            260                 265                 270

Leu Asp Val Ala Asn Val Thr Asp Pro Ser Thr Leu Ala Leu Leu Ala
        275                 280                 285

Thr Gly Ala Val Met Ile Asn Arg Ala Ser Gly Gln Asn Asp Gly Leu
    290                 295                 300

Val Ser Arg Cys Ser Ser Leu Phe Gly Gln Val Ile Ser Thr Ser Tyr
305                 310                 315                 320

His Trp Asn His Leu Asp Glu Ile Asn Gln Leu Leu Gly Val Arg Gly
                325                 330                 335

Ala Asn Ala Glu Asp Pro Val Ala Val Ile Arg Thr His Val Asn Arg
            340                 345                 350
```

```
Leu Lys Leu Gln Gly Val
        355

<210> SEQ ID NO 3
<211> LENGTH: 353
<212> TYPE: PRT
<213> ORGANISM: Burkholderia plantarii

<400> SEQUENCE: 3

Met Ala Gln Ala Asp Arg Pro Ala Arg Gly Gly Leu Ala Ala Arg Pro
1               5                   10                  15

Met Arg Gly Ala Ser Phe Ala Leu Ala Gly Leu Val Ala Cys Ala Ala
            20                  25                  30

Cys Ala Ala Val Val Leu Trp Leu Arg Pro Ala Ala Pro Ser Pro Ala
        35                  40                  45

Pro Ala Gly Ala Val Ala Gly Gly Pro Ala Ala Gly Val Pro Ala Ala
    50                  55                  60

Ala Ser Gly Ala Ala Glu Ala Ala Met Pro Leu Pro Ala Ala Leu Pro
65                  70                  75                  80

Gly Ala Leu Ala Gly Ser His Ala Pro Arg Leu Pro Leu Ala Ala Gly
                85                  90                  95

Gly Arg Leu Ala Arg Thr Arg Ala Val Arg Glu Phe Phe Asp Tyr Cys
            100                 105                 110

Leu Thr Ala Gln Gly Glu Leu Thr Pro Ala Ala Leu Asp Ala Leu Val
        115                 120                 125

Arg Arg Glu Ile Ala Ala Gln Leu Asp Gly Ser Pro Gln Ala Glu
    130                 135                 140

Ala Leu Gly Val Trp Arg Arg Tyr Arg Ala Tyr Phe Asp Ala Leu Ala
145                 150                 155                 160

Gln Leu Pro Gly Asp Gly Ala Val Leu Gly Asp Lys Leu Asp Pro Ala
                165                 170                 175

Ala Met Gln Leu Ala Leu Asp Gln Arg Ala Ala Leu Ala Asp Arg Thr
            180                 185                 190

Leu Gly Glu Trp Ala Glu Pro Phe Phe Gly Asp Glu Gln Arg Arg Gln
        195                 200                 205

Arg His Asp Leu Glu Arg Ile Arg Ile Ala Asn Asp Thr Thr Leu Ser
    210                 215                 220

Pro Glu Gln Lys Ala Ala Arg Leu Ala Ala Leu Asp Ala Gln Leu Thr
225                 230                 235                 240

Pro Asp Glu Arg Ala Gln Gln Ala Ala Leu His Ala Gln Asp Ala
                245                 250                 255

Val Thr Lys Ile Ala Asp Leu Gln Lys Ala Gly Ala Thr Pro Asp Gln
            260                 265                 270

Met Arg Ala Gln Ile Ala Gln Thr Leu Gly Pro Glu Ala Ala Arg
        275                 280                 285

Ala Ala Gln Met Gln Gln Asp Asp Glu Ala Trp Gln Thr Arg Tyr Gln
    290                 295                 300

Ala Tyr Ala Ala Glu Arg Asp Arg Ile Ala Ala Gln Gly Leu Ala Pro
305                 310                 315                 320

Gln Asp Arg Asp Ala Arg Ile Ala Gln Leu Arg Gln Gln Thr Phe Thr
                325                 330                 335

Ala Pro Gly Glu Ala Ile Arg Ala Ala Ser Leu Asp Arg Gly Ala Gly
            340                 345                 350

Gly
```